United States Patent [19]
Proctor

[11] Patent Number: 5,370,680
[45] Date of Patent: Dec. 6, 1994

[54] ATHERMAPEUTIC APPARATUS EMPLOYING ELECTRO-MAGNETIC FIELDS

[75] Inventor: Eugene V. Proctor, Lomita, Calif.

[73] Assignee: Magnetic Resonance Therapeutics, Inc., Pompano Beach, Fla.

[21] Appl. No.: 889,504

[22] Filed: May 27, 1992

[51] Int. Cl.$^5$ .............................. A61N 1/06
[52] U.S. Cl. .................... 607/154; 607/71; 607/115
[58] Field of Search ............ 128/422, 802, 804; 607/115, 149, 154, 155, 100, 101, 103, 71; 600/14

[56] References Cited

U.S. PATENT DOCUMENTS

| | | | |
|---|---|---|---|
| 1,233,841 | 7/1917 | Butcher | 128/422 X |
| 2,130,758 | 9/1938 | Rose | 128/804 |
| 2,648,727 | 8/1953 | Rockwell | 128/422 |
| 3,043,310 | 7/1962 | Milchowski | 128/422 |
| 3,181,535 | 5/1965 | Milinowski | 128/422 |
| 3,270,746 | 9/1966 | Kendall et al. | 128/804 |
| 3,329,148 | 7/1967 | Kendal | 128/422 |
| 3,978,864 | 9/1976 | Smith et al. | 128/804 |
| 4,028,518 | 6/1977 | Boudouris et al. | 128/804 X |

OTHER PUBLICATIONS

Radio Shack New 1978-79 Unabridged Dictionary of Electronics p. 107.

Primary Examiner—Lee S. Cohen
Assistant Examiner—Jeffrey R. Jastrzab
Attorney, Agent, or Firm—M. K. Silverman

[57] ABSTRACT

Medical athermapeutic apparatus employing pulsed electromagnetic fields includes solid state regulator and power amplifier circuits and simplified applicator which result in reduced size, cost and power consumption for the device.

5 Claims, 4 Drawing Sheets

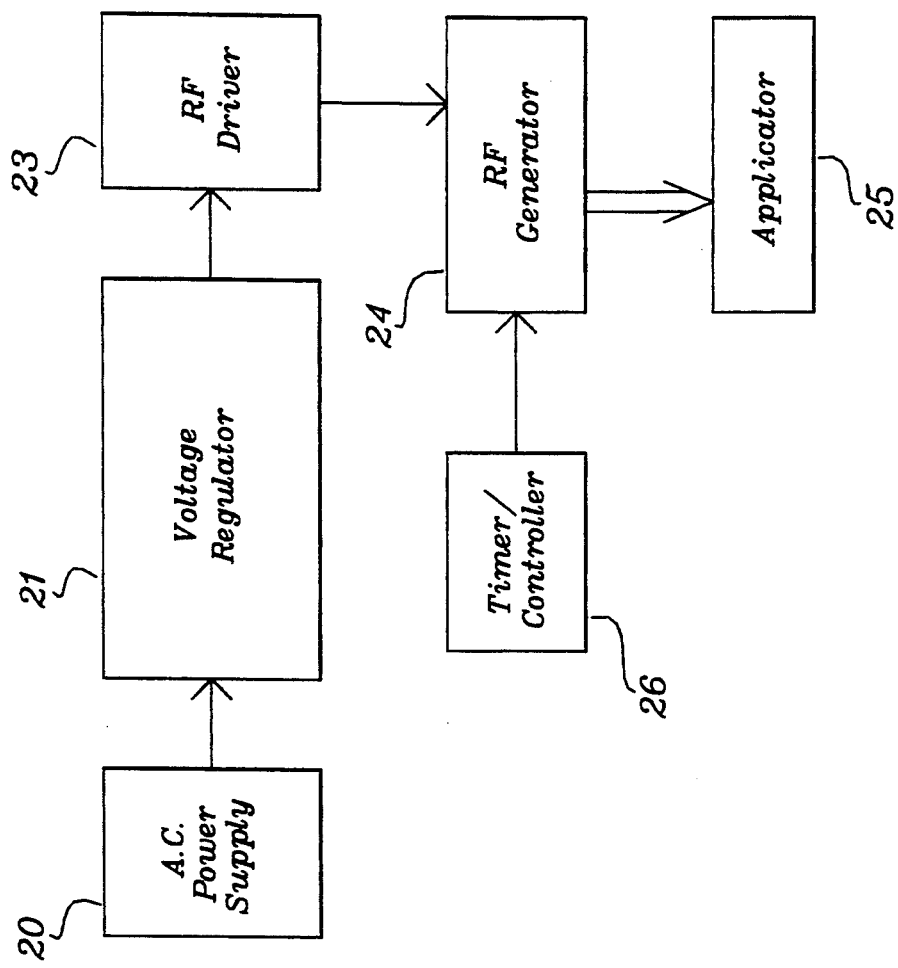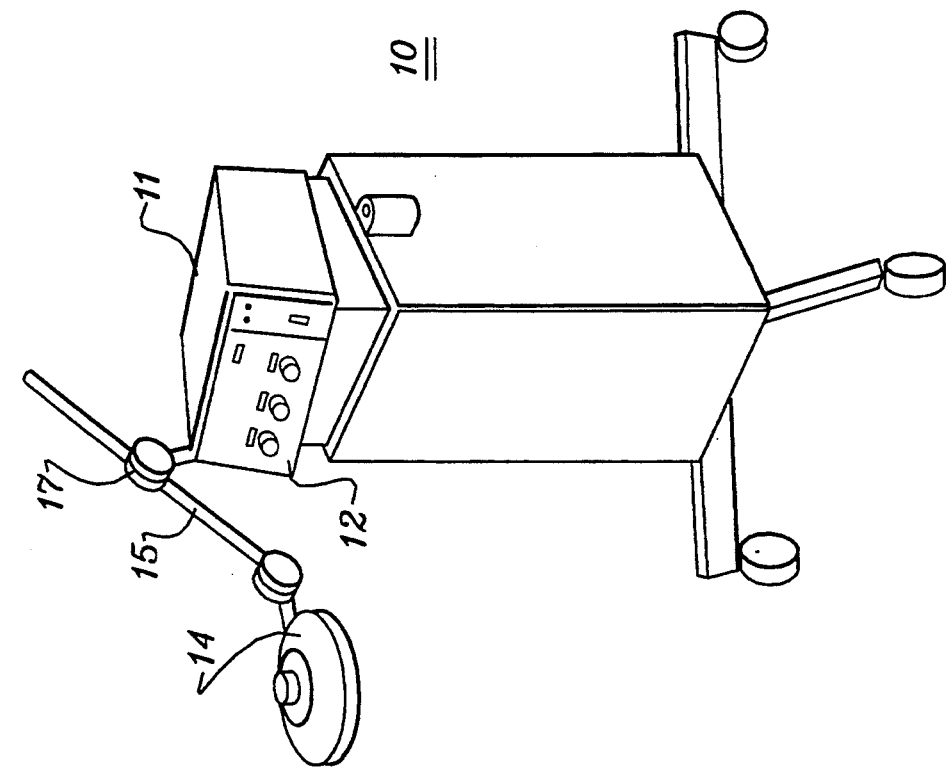

ATHERMAPEUTIC APPARATUS EMPLOYING ELECTRO-MAGNETIC FIELDS

FIELD OF THE INVENTION

This invention relates to medical therapeutic apparatus and more particularly to such apparatus which employs Pulsed Electromagnetic Field Therapy (PEMF) to promote the healing of bone and soft tissue injuries.

BACKGROUND OF THE INVENTION

Athermapeutic apparatus employing Pulsed Electromagnetic Fields are known. One such device is disclosed in U.S. Pat. No. 3,181,535 issued May 4, 1965. Athermapeutic apparatus of this type produces a pulsed field which provides a negative charge to injured tissue. When applied soon after injury, or surgery, the field restores normal electrical charge across cell membranes, a charge which is interrupted by injury. With the restoration of normal charge at the cell level, a body's mostly chemical healing process is promoted. The result is quicker healing with less swelling and pain.

Presently available athermapeutic devices of this type are bulky and require relatively large amounts of power.

BRIEF DESCRIPTION OF AN ILLUSTRATIVE EMBODIMENT OF THIS INVENTION

The present invention is directed at an athermapeutic apparatus including solid state electronics which requires less power and is relatively compact and easier to use. The electronics include a voltage regulator which permits tight regulation taking advantage of unusual requirements of the system that high amplitude pulses have to be delivered over a very short duty cycle.

The circuitry also includes an output power amplifier which combines power from six transistors organized in pushpull pairs, each pair being connected to a transformer. The three transformer secondaries are combined in series thus producing a parallel to series power converter.

Athermapeutic apparatus of the type described herein include an applicator by means of which energy is introduced into a body. The applicator includes a pair of capacitors which in prior devices are oriented in a plane perpendicular to the plane of the applicator and thus perpendicular to the plane of the body. The perpendicular orientation of the capacitor is to ensure that a patient's body capacitance does not add to the applicator capacitance to disturb the adjustment of the applicator capacitance during treatment.

In accordance with the principles of the present invention, a butterfly type capacitor is employed and is oriented in the plane of the applicator in a manner to employ a patient's body capacitance during treatment. The reorientation of the capacitor into the plane of the applicator, the use of a butterfly capacitor in an orientation to use of a patient's body capacitance as well as the regulator and output power amplified circuits are considered significant departures from prior art thinking. The result of the capacitor reorientation and construction along with the regulator and amplifier design allow not only an applicator of reduced size to be achieved but the realization of a considerable reduction in size, power consumption, and cost of the system.

BRIEF DESCRIPTION OF THE DRAWINGS

FIG. 1 is a perspective view of an athermapeutic device in accordance with the principles of this invention;

FIG. 2 is a block diagram of the electronics for the device of FIG. 1;

DETAILED DESCRIPTION OF AN ILLUSTRATIVE EMBODIMENT OF THIS INVENTION

Figure 3:
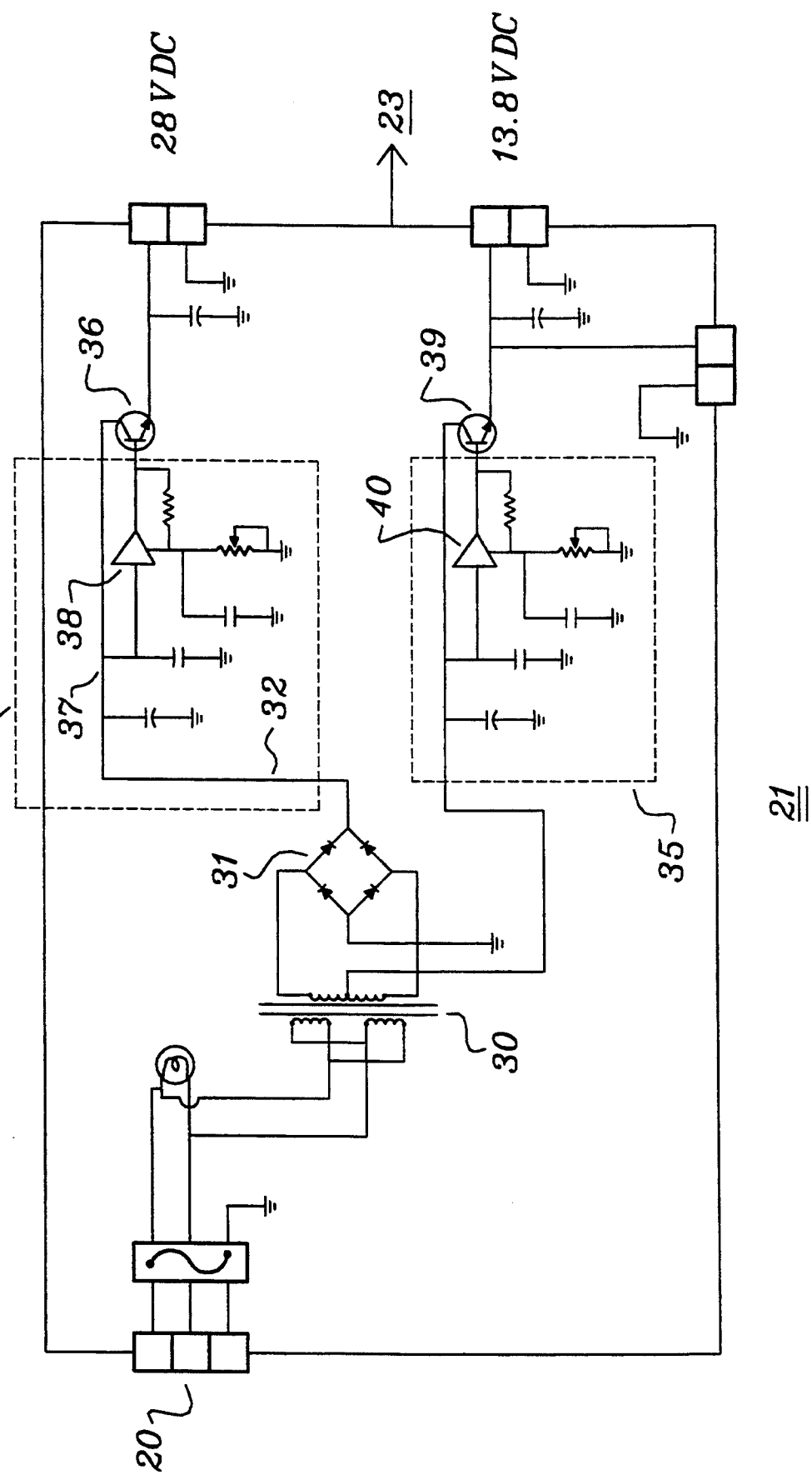
FIG. 3 and FIG. 4 are circuit schematics for voltage regulator and R.F. driver portions respectively of the block diagram of FIG. 2.

FIG. 1 shows an athermapeutic device 10 in accordance with this invention. The device includes a housing 11 with a control panel 12 for operator use. The device also includes an applicator 14 attached to an arm 15. Arm 15 is connected to an adjustment assembly at 17 for rotary and axial adjustment. The entire device is on wheels, as shown for ease of movement and is intended for placement over a patient (not shown) who would be lying on a table.

FIG. 2 shows a block diagram of the electronic circuitry for the device of FIG. 1. The circuitry includes an alternating current (AC) supply represented by block 20 and a regulator 21 for that supply. The voltage output of the regulator is applied to a radio frequency (RF) circuitry driver 23. The RF output of driver 23 is applied to RF generator 24 which drives applicator 25.

Applicator 25 includes a butterfly capacitor for controlling the energy generated by the applicator as will be discussed more fully below. The RF generator is controlled by time and controller 26, under operator control at panel 12 in FIG. 1.

The various circuit components of FIG. 2 generally are conventional and function in a manner analogous to that described in the above mentioned patent. But the circuit for regulation of the input power and the circuit for generating output power are unique and take advantage of the relaxed nature of the output energy constraints of athermapeutic apparatus of this type to achieve significant reductions in size and cost of the equipment.

Specifically, FIG. 3 shows the input power regulation circuit schematic for regulator 21 of FIG. 2 for supplying both 28 volt DC and 13.8 volt DC required illustratively by the RF circuit driver 23 of FIG. 2. The circuit includes a transformer 30 to the primary winding of which the raw AC power is supplied. The transformer provides the desired voltage at its secondary. A bridge rectifier 31 is connected across the secondary of the transformer to provide a direct current supply along line 32.

First and second regulator circuits 34 and 35 operate to regulate only the base voltages of transistors 36 and 39 respectively. Specifically, regulator circuit 34 is connected between bridge 31 and the emitter of transistor 36 via line 37 and between the bridge and the base of transistor 36 via amplifier 38. The regulator also includes various capacitors and resistors which are conventional in regulators and are operative to adjust the amplitude and duration of the voltage pulse in a well understood manner.

Regulator circuit 35 is analogous to regulator 34 except that it is connected from the center tap of the transformer 30 secondary to the emitter of transistor 39 and connected from that center tap to the base of transistor 39 via amplifier 40. Regulator circuit 34 produces a 28 volt DC output, regulator circuit 35 produces a 13.8 volt DC output.

The regulation of only the input to base voltage rather than the normal regulation of from the output to the input (collector to emitter) is adequate because the apparatus power requirements demand relatively less precision than usual because of the high power peaks delivered by the apparatus and the short duty cycles as will be explained more fully below. Because satisfactory regulation can be provided from emitter to base, only twenty percent of the work is performed by the regulator at a significant cost savings for regulation. The cost advantage arises because relatively low cost commercial regulators are available even though high power regulation is required. The input and output capacitors in the regulator are merely to supply power when the 60 hertz input is absent and when charge is absent respectively.

Figure 4:
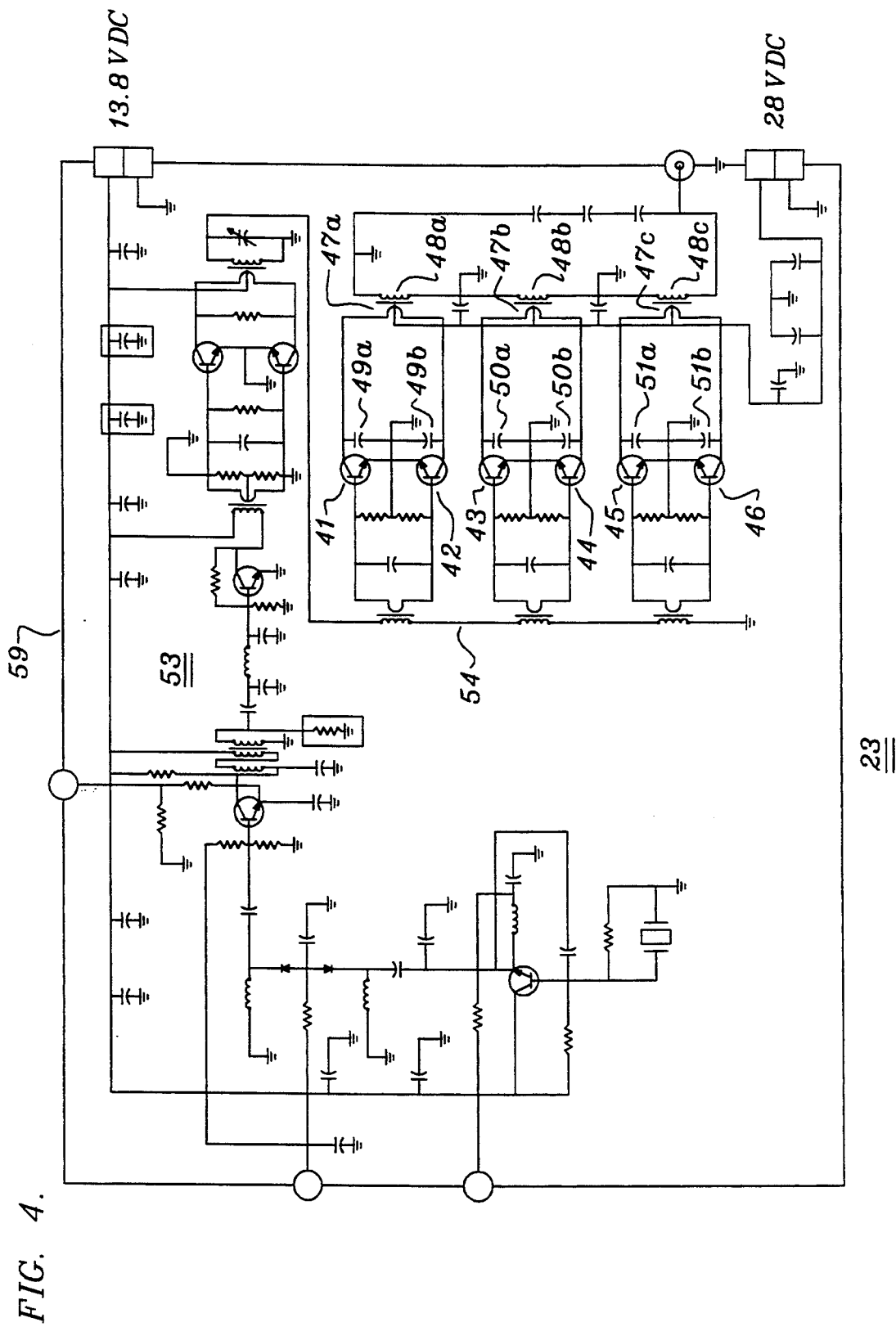

The 13.8 VDC and 28 VDC outputs from regulator circuits 34 and 35 are applied to inputs to the RF output stage including the power amplifier shown in FIG. 4. Specifically, FIG. 4 shows RF driver 23 of FIG. 2 including six transistors 41, 42, 43, 44, 45, and 46 connected in an emitter follower configuration. The transistors are arranged in pairs, 41-42, 43-44, 45-46, in a push-pull fashion. The emitters of each pair are connected across transformers 47A, 47B, and 47C. The secondaries, 48A, 48B, and 48C, are connected in series thus producing a parallel to series power converters. The emitters of each pair also are connected across capacitors 49A-49B, 50A-50B, and 51A-51C respectively, as shown. The collectors of each transistors pair are connected to ground as is one plate of each capacitor of the associated pair of capacitors.

The 28 VDC supply from regulator circuit 34 of FIG. 3 is applied to a center tap of primary windings of transformers 47A, 47B, and 47C the 13.8 VDC from regulator circuit 35 of FIG. 3 is applied to a conventional oscillator and preamp 53 to precondition the pulses to a form suitable for amplification herein in a well understood manner. The preamp includes a driver second stage and a push-pull driver stage of conventional design to generate three watts (RMS) with fifty watts peak power along line 54 of FIG. 4.

The RF output stage for athermapeutic apparatus requires a well regulated voltage supply (better than 2 percent) capable of delivering very high peak currents (in excess of fifty amperes) but with a duty cycle of only a few percent. The pulse is supplied for only sixty five microseconds out of every sixteen hundred and sixty seven microseconds, worst case. In conventional regulated supply, the output is sensed by the circuitry. In the present apparatus, the actual output stage of FIG. 4 is an emitter follower transistor network driving storage capacitors capable of handling the peak currents with only a small amount of sag.

The base of each emitter follower transistor of FIG. 4 is driven by an adjustable regulated supply, and the collector is maintained at the raw DC supply level. Each capacitor handles the high current peaks. Each emitter follower recharges the associated capacitor between peaks and the regulator 34 determines the approximate voltage.

The output power amplifier is capable of delivering 1000 peak watts using a relatively low voltage power supply. Various other components of a practical embodiment of the invention are used for timing, loading and the proper Q as is well understood in the art.

The total error introduced by the emitter follower configuration that is not adjusted out consists mainly of two components: The first of these is a temperature dependent variability of the emitter - base function which is approximately two millivolts per degree centigrade and the current dependent variability of the same function. The latter is approximately seventy millivolts per decade of current. The total error represents less than about two percent of the pulse delivered to generator 24 of FIG. 2. Generator 24 provides the RF pulses with the proper amplitude and frequency for applicator 25 under the control of timer and controller 26.

Figure 6:
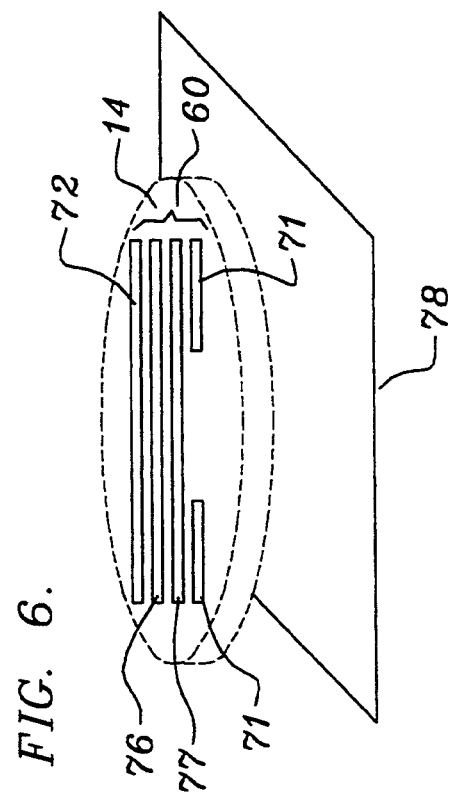
FIG. 5 and FIG. 6 are top and side views of a butterfly capacitor useful in accordance with this invention.
Figure 5:
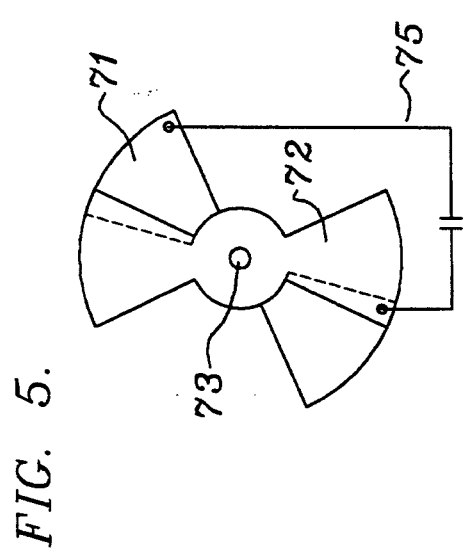

FIGS. 5 and 6 show top and side views of a butterfly capacitor 60. The capacitor resides in applicator 14 as indicated. The capacitor includes two parallel shaped metal plates 71 and 72, the first of which (the rotor plate) is rotatable with respect to the other (stator) about a common shaft 73. The plates are connected electronically in series by line 75 and the capacitance between the plates is regulated by rotating the rotor and is determined by the amount of overlap between the plates as is well understood. The affected part of a patient in plane 78 of FIG. 8 becomes a portion of the rotor plate of the tuning capacitor. The plates are separated by two insulating layers 76 and 77 as is common. The use of a butterfly capacitor and the orientation of the plane of the capacitor in parallel with an affected body part maximizes effective energy transfer to the body part and minimizes the standing wave ratio (SWR).

What is claimed is:

1. Athermapeutic apparatus for inducing electrical charge in the cells of a patient, said apparatus including an applicator for producing pulsed electromagnetic fields in a selected portion of the body of said patient, said fields being generated at a selected frequency, amplitude and duration, said applicator having a large area face in a first plane to be placed facing the patient, said applicator including a variable capacitor having first and second parallel plates, said plates being oriented in planes parallel to said first plane, said apparatus including means operative to vary capacitance between said parallel plates for varying the frequency of said pulses wherein said variable capacitor is of a butterfly type, said first and second plates comprising a rotor and a stator respectively, and said means operative to vary the capacitance comprising means for rotating said rotor with respect to said stator.

2. Athermapeutic apparatus as set forth in claim 1 also including means for setting the amplitude and duration of said pulsed electromagnetic fields radiated by said applicator.

3. Athermapeutic apparatus as set forth in claim 2 including a power stage connected to said applicator, said stage including a plurality of pairs of transistors, each of said transistors having an emitter base, and a collector, said stage also including a plurality of transformers each having primary and secondary windlass and a center tap and being associated with one of said pairs of transistors, said emitters of the transistors of each of said pairs being connected across the primary winding of an associated one of said transformers, the secondary windings of said transformers being connected in series, said apparatus including means for applying a first voltage to the bases of aid transistors and means for operating each of said pairs in a push pull manner.

4. Athermapeutic apparatus as set forth in claim 3 wherein said means for applying said first voltage comprises a first transistor having an emitter, base, and collector and means connected between said emitter and said base for regulating a voltage at said base.

5. Athermapeutic apparatus as set forth in claim 4 wherein a second voltage is applied to said center tap in each of said primary windings.

* * * * *